United States Patent [19]
Gray, III

[11] Patent Number: 5,800,555
[45] Date of Patent: Sep. 1, 1998

[54] ACETABULAR CUP BEARING LINER

[75] Inventor: Frederick C. Gray, III, Winona Lake, Ind.

[73] Assignee: DePuy Orthopaedics, Inc., Warsaw, Ind.

[21] Appl. No.: 842,074

[22] Filed: Apr. 24, 1997

[51] Int. Cl.[6] ............................................ A61F 2/32
[52] U.S. Cl. ................................... 623/22; 623/18
[58] Field of Search ......................... 623/22, 23, 18

[56] References Cited

U.S. PATENT DOCUMENTS

| | | | |
|---|---|---|---|
| 4,380,090 | 4/1983 | Ramos | 623/22 |
| 4,524,467 | 6/1985 | De Carlo, Jr. | 623/22 |
| 4,642,123 | 2/1987 | Noiles | |
| 4,676,798 | 6/1987 | Noiles | |
| 4,678,472 | 7/1987 | Noiles | |
| 4,798,610 | 1/1989 | Averill et al. | 623/22 |
| 4,919,674 | 4/1990 | Schelhas | 623/22 |
| 4,936,855 | 6/1990 | Sherman | 623/22 |
| 4,950,299 | 8/1990 | Noiles | |
| 4,960,427 | 10/1990 | Noiles | |
| 4,978,356 | 12/1990 | Noiles | |
| 5,019,105 | 5/1991 | Wiley | 623/22 |
| 5,049,158 | 9/1991 | Engelhardt et al. | |
| 5,062,853 | 11/1991 | Forte | 623/22 |
| 5,156,626 | 10/1992 | Broderick et al. | 623/22 |
| 5,263,988 | 11/1993 | Huebner | 623/22 |
| 5,314,491 | 5/1994 | Thongpreda et al. | 623/22 |

*Primary Examiner*—Michael J. Milano
*Assistant Examiner*—Tram Anh T. Nguyen
*Attorney, Agent, or Firm*—Barnes & Thornburg

[57] ABSTRACT

A bearing liner component for a ball-and-socket joint prosthesis is described. The bearing component comprises a bearing liner and locking component. The bearing liner is formed with a rim that defines an opening to a concave bearing surface that describes more than a hemisphere. The bearing liner is further provided with a lip extending around the rim and a channel formed in the lip. The channel is formed to permit elastic deformation of the bearing liner around the rim sufficient to permit elastic deformation of the bearing liner around the rim to allow a ball prosthesis with generally the same diameter as the bearing surface to enter the bearing liner. A locking component is also provided that couples the lip of the bearing liner to inhibit elastic deformation of the bearing surface around the rim.

35 Claims, 2 Drawing Sheets

ACETABULAR CUP BEARING LINER

BACKGROUND AND SUMMARY OF THE INVENTION

The present invention relates to an improved bearing liner for a ball-and-socket prosthesis that resists dislocation of the ball from the socket by providing a generally spherical cavity that encloses more than half of the ball. More particularly, the present invention relates to a single bearing liner that lacks breaks or cuts in the bearing surface and encloses more than half of the prosthetic femoral ball upon insertion of the ball into the cavity of the bearing liner.

Luxation can cause problems with ball-and-socket prostheses. It is therefore desirable to design a bearing liner that inhibits dislocation of the ball from its socket in prosthetic ball-and-socket joints. One design that decreases the chance of ball dislocation is a bearing liner that encloses more than a half of the ball within a hemisphere shaped cavity of the bearing liner. Bearing designs that enclose more than half the ball within the bearing liner have been previously described and typically either use multiple bearing liner components that can assemble around the ball, or employ a single bearing liner component with breaks or cuts in its surface to allow expansion of the opening to the bearing liner cavity while the ball is forced into the liner cavity. Such conventional designs suffer from several disadvantages. For example, bearing designs that require multiple components add to the cost of manufacture (due to the need for specific tolerances between multiple sections of the bearing surface). Therefore, a continuous bearing liner that encloses more than half of the ball is highly desirable.

According to the present invention, the bearing component comprises a bearing liner and a locking component configured to inhibit the elastic deformation of an opening to a bearing liner cavity. The bearing liner includes a rim that defines the opening to the bearing liner cavity. In one embodiment, the bearing liner cavity is concave in shape and of sufficient size that over half of a femoral ball fits within the bearing liner cavity. The bearing liner is further provided with means for permitting elastic deformation of the bearing surface around the rim of the bearing liner, wherein the deformation enlarges the opening to the concave bearing surface. In accordance with one embodiment, the locking component is formed to fit around the rim of the bearing liner to inhibit elastic deformation of the bearing surface around the rim.

In accordance with one embodiment of the bearing liner, an outer face is located at the opening to the bearing liner cavity and is formed to include a concentric channel defining a first radially inner and a second radially outer concentric extension. The inner surface of the first extension forms an integral portion of the inner articular surface, and is provided with a rim. The rim defines the opening to the bearing liner cavity. The first extension is designed to be flexible toward the second extension so that a biasing force will deform the first extension allowing the enlargement of the opening to the bearing liner cavity. Upon removal of the biasing force the first extension returns to its original position. A ball having a diameter greater than the diameter of the opening of the bearing liner can be inserted into the bearing liner cavity of that bearing liner. As the ball is pushed through the opening of the bearing liner, the first extension will be moved toward the second extension, decreasing the width of the channel formed between the first and second extensions. After complete insertion of the ball into the bearing liner cavity, the first extension will return to its original position to hold the ball within the bearing liner cavity.

In one embodiment, the bearing liner further comprises means for securing the ball within the bearing liner cavity. Once the ball has been inserted in the bearing liner cavity, preventing the first extension from being moved toward the second extension will prevent enlargement of the opening and will effectively lock the ball within the bearing liner cavity. In one embodiment, a securing ring having similar dimensions as the channel is placed into the channel to frictionally engage the outer surface of the first extension and the inner surface of the second extension. In this manner the opening to the bearing liner cavity cannot be expanded to release the ball.

In an alternative embodiment, the securing ring can be formed to have a first end having a width equal or smaller than the width of the channel and a second end having a width greater than the width of the channel. In this embodiment, insertion of the securing ring into the channel biases the first extension away from the second extension, thus narrowing the opening to the bearing liner cavity.

In one preferred embodiment of the present invention, the bearing component is formed with an outer surface that is generally concentric with the bearing liner cavity. This embodiment is suitable for use with a socket housing with an opening such as the acetabular cup of U.S. Pat. No. 5,049,158. The bearing component includes a groove formed near a meridian in the outer surface that is axially aligned with the opening to the cavity of the bearing. The groove of the bearing aligns with a groove in the opening of the socket housing upon full insertion of the bearing into the socket housing. A lock wire engages the grooves in both the bearing and socket housing when the bearing is fully inserted into the socket housing. Anti-rotation lugs can be formed on the inner surface of the socket housing, where the lugs interfere or machine into the bearing as the bearing is inserted into the socket housing.

Additional objects, features and advantages of the invention will become apparent to those skilled in the art upon consideration of the following detailed description of a preferred embodiment exemplifying the best mode of carrying out the invention as presently perceived.

DETAILED DESCRIPTION OF THE DRAWINGS

Figure 1:
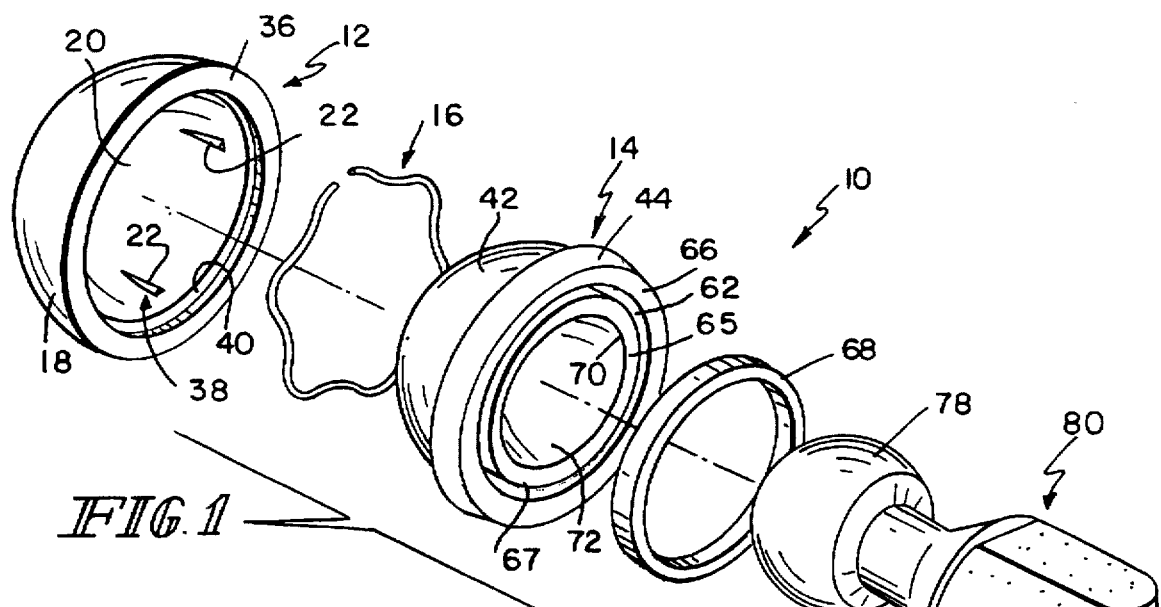
FIG. 1 is an exploded perspective view of a preferred embodiment of the present invention illustrating a hip prosthesis assembly comprising a lock wire positioned between a socket housing and a bearing liner, and a securing ring positioned between the bearing liner and a femur stem with a ball.

Referring to the drawings and particularly to FIG. 1, it will be seen that assembly 10 provides a single piece bearing liner that encloses more than half of a ball, wherein the diameter of the entrance to the cavity of the bearing liner is smaller than the diameter of the prosthetic ball, without requiring any cuts or breaks in the bearing surface of the liner. The desired effect is obtained through the use of an extension that forms the entrance to the cavity wherein the extension is elastically deformable to allow insertion of the ball into the cavity. The bearing component is further provided with inhibiting means that prevent elastic enlargement of the opening to the cavity of the liner after the ball is inserted into the liner cavity. The bearing component of the present application can be used in combination with an acetabular cup assembly for replacement of natural ball-and-socket joints. In particular the present bearing component is compatible with the invention in U.S. Pat. No. 5,049,158 entitled "Acetabular Cup Assembly", by inventors John A. Englehardt et al., the disclosure of which is expressly incorporated herein by reference.

In particular, assembly 10 comprises an acetabular cup or socket housing 12 designed to be affixed in the acetabulum to replace the natural hip socket of a patient and a bearing liner 14 designed to be inserted into the acetabular cup 12 as taught in U.S. Pat. No. 5,049,158, the disclosure of which is expressly incorporated herein by reference. A lock wire 16 is provided to retain the bearing liner 14 within the acetabular cup 12. The acetabular cup 12 includes an outer surface 18 and a generally hemispherically shaped inner surface 20. The inner surface 20 of acetabular cup 12 is provided with a plurality of anti-rotation lugs 22 which engage an outer surface 42 of the bearing liner 14 upon insertion of the bearing liner 14 into acetabular cup 12. The acetabular cup 12 has a lip or rim 36 through which the bearing liner 14 enters a cavity 38 formed by inner surface 20. Arcuate groove 40 extends around the periphery of cavity 38 spaced apart from rim 36 by a predetermined distance.

Bearing liner 14 includes the generally hemispherical convex outer surface 42 which is congruent or complimentary to inner surface 20. Bearing liner 14 further includes an annular flange 44 which abuts the rim 36 when the bearing liner 14 is fully inserted into the acetabular cup 12 and an annular groove 52 formed in the convex surface outer surface 42 such that the annular groove 52 aligns with the arcuate groove 40 of the acetabular cup 12 when the bearing liner 14 is fully inserted in the acetabular cup 12. (See FIG. 2) Lock wire 16 is inserted into the arcuate groove 40 of acetabular cup 12 prior to insertion of the bearing liner 14 into the acetabular cup 12 and engages both the annular groove 52 and the arcuate groove 40 when the annular groove 52 aligns with the arcuate groove 40. Essentially, as taught by U.S. Pat. No. 5,049,158, wire 16 has radially outwardly extending lobes which engage into groove 40 and radially inwardly extending lobes which engage into groove 52. The spring-like nature of the wire 16 provides a snap-ring which holds the bearing liner 14 in the cup 12. While the lock wire 16 is illustrated and described, it will be understood that other locking elements may be used to retain the bearing liner 14 within the acetabular cup 12.

Figure 2:
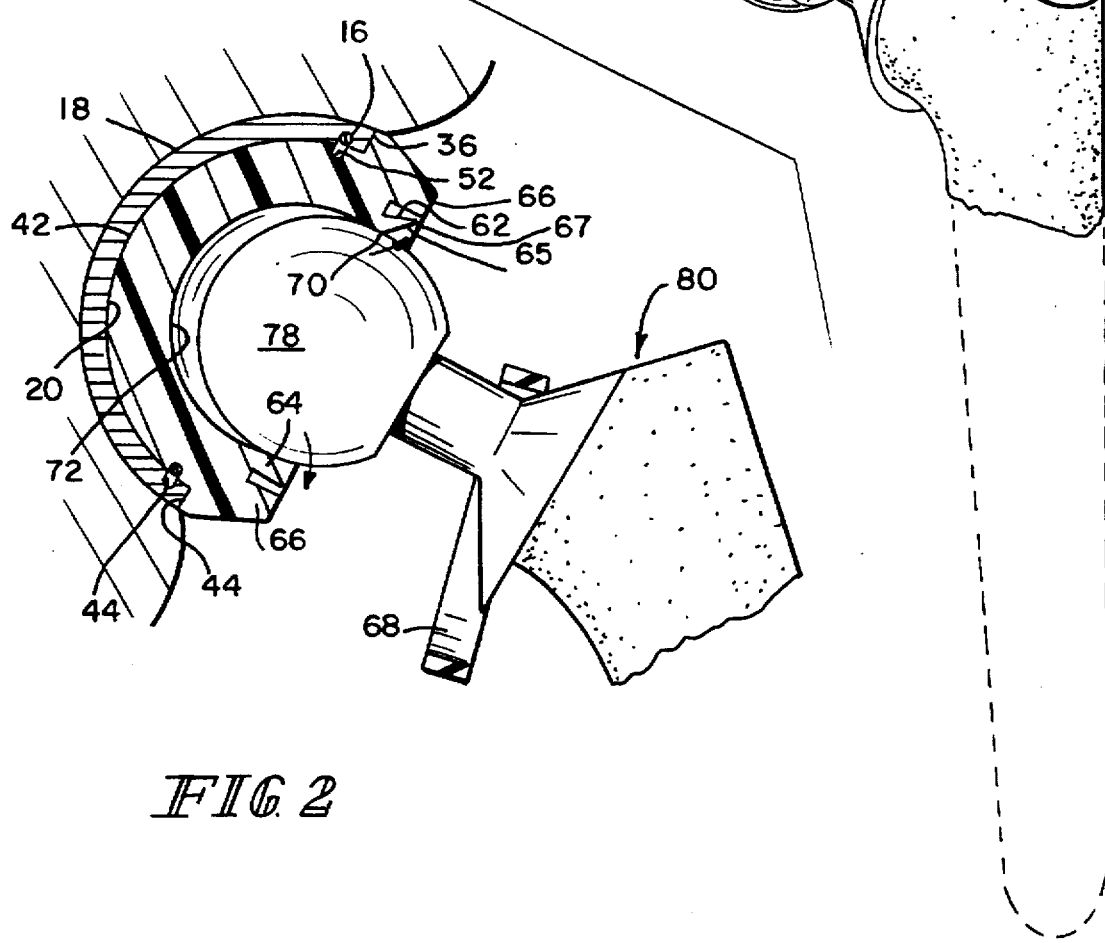
FIG. 2 is a sectional view illustrating insertion of the ball into the bearing liner, the bearing liner situated within the socket housing and the lock wire situated inside arcuate grooves formed in both the bearing liner and the socket housing.

The outer surface 42 of the bearing liner 14 is provided with an annular channel 62 generally concentric with the bearing liner cavity 72 and defining a first concentric annular extension 64 and a second concentric annular extension 66. The inner surface of first annular extension 64 is provided with an annular rim 70 that defines the opening to the bearing liner cavity 72 of the bearing liner 14. The first annular extension has a ramp portion 65 leading to its outer lip 67. Channel 62 is formed for receiving a securing ring 68 that frictionally engages a radially inner surface of second annular extension 66 and a radially outer surface of first annular extension 64 and prevents the first annular extension 64 from being biased toward the second annular extension 66. Prior to insertion of securing ring 68, a ball 78 on a femur stem 80 will move the first annular extension 64 toward the second annular extension 66 during insertion of the ball 78 into bearing liner cavity 72 of the bearing liner 14, as shown in FIG. 2. Insertion of the securing ring 68 into the annular channel 62 fixes the ball 78 in place in the bearing liner cavity 72 of the bearing 14. It will be seen that the bearing liner cavity 72 has a shape that is greater than hemispherical, such that the ball 78 will be captured in the bearing liner cavity 72 when the first annular extension 64 is secured against radially outward movement by the insertion of the securing ring 68 into the channel 62.

Bearing liner 14 is formed from a conventional plastic suitable for implantation and having sufficient flexibility to allow elastic deformation of the first annular extension 64 to allow entry of the inelastic ball 78 into the bearing liner cavity 72 prior to insertion of the securing ring 68. The bearing liner cavity 72 encloses more than half of the ball 78 to restrain dislocation of the ball 78 from the bearing liner cavity 72. The securing ring 68 prevents elastic deformation of the first annular extension 64 and thereby prevents dislocation of the ball 78. While a securing ring 68 is illustrated and described, it will be understood that other expansion elements may be used to restrict radially outward movement of the first extension 64 and thus secure the ball 78 within the bearing liner cavity 72.

Figure 3:
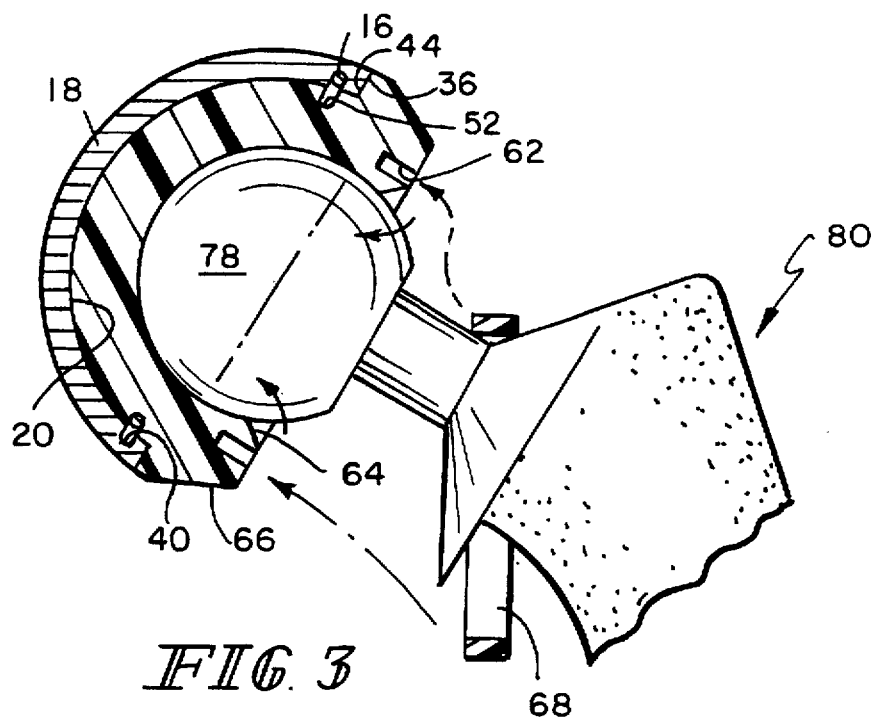
FIG. 3 is a sectional view showing the installation of the securing ring after full insertion of the ball into the bearing liner.
Figure 4:
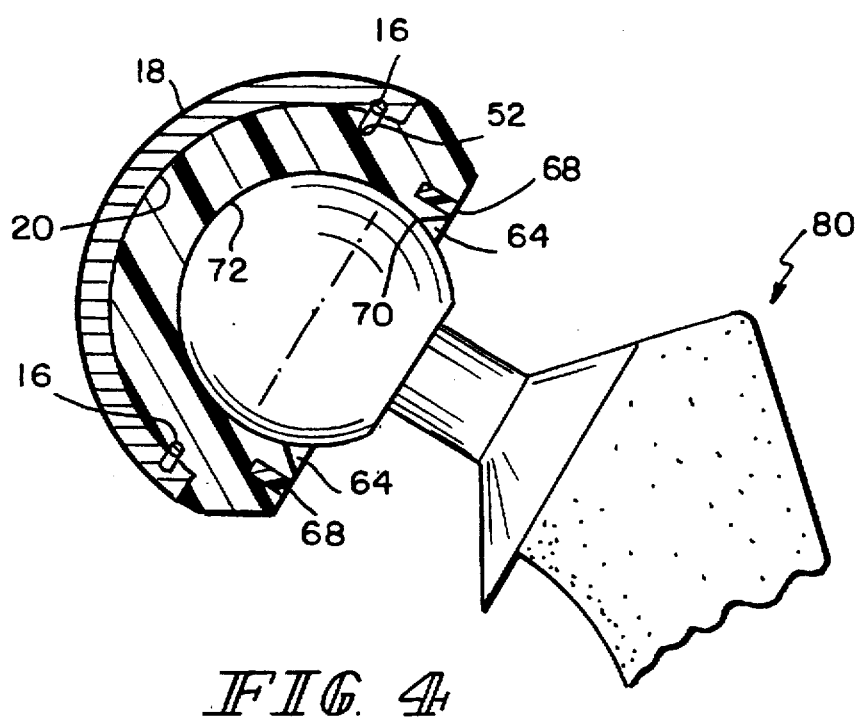
FIG. 4 is a sectional view illustrating the fully assembled prosthesis.

FIGS. 2–4 illustrate the assembly of the prosthetic joint incorporating a preferred embodiment of the present invention. The ball 78 is first inserted through the securing ring 68 prior to insertion into the bearing liner cavity 72. The securing ring 68 has a diameter greater than that of the ball 78 such that the securing ring 68 hangs from the femur stem 80 during insertion of the ball 78 into the bearing liner cavity 72, as best shown in FIGS. 2 and 3. FIG. 2 shows the inelastic prosthetic ball 78 being inserted into the bearing liner cavity 72. In a preferred embodiment, the bearing liner 14 is manufactured from a material such as ultra high molecular weight polyethylene, allowing radially outward elastic deformation of the first annular extension 64 as the inelastic ball 78 is inserted into the bearing liner 72. It is understood that another suitable material or combination of materials can be used in the place of ultra high molecular weight polyethylene to achieve a similar effect in the present invention. As the ball 78 is forced against the annular rim 70 that defines the opening to the bearing liner cavity 72, the first annular extension 64 is moved towards the second annular extension 66 enlarging the opening defined by the annular rim 70 until it is approximately the diameter of the ball 78, at which time the ball 78 can fully enter the bearing liner cavity 72 as shown in FIG. 2. After full entry of the ball 78 into the bearing liner cavity 72, the first annular extension 64 elastically returns to its original position, as best shown in FIG. 3.

As shown in FIGS. 3–4, the ball 78 is retained in the bearing liner cavity 72 by insertion of the securing ring 68 into the annular channel 62. After the securing ring 68 is fully inserted in the annular channel 62, as shown in FIG. 4, the first annular extension 64 is prevented from moving towards the second annular extension 66 and the annular rim 70 resists dislocation of the ball 78 from the bearing liner cavity 72.

One feature of the present invention is the provision for a single bearing liner with a bearing surface without joints between separate pieces or breaks in the bearing surface. A unitary, unbroken design provides the benefit of simplified manufacturing. The bearing liner is formed to allow elastic deformation of the liner sufficient to allow an inelastic ball with a diameter generally the same as the bearing liner cavity to pass through the opening and into the bearing liner cavity.

Another feature of the present invention is means for inhibiting elastic deformation of the first annular extension (defining the opening to the bearing liner cavity) after the ball is placed in the bearing liner cavity. By restraining the elastic deformation of the first annular extension forming the opening to the bearing liner cavity, the prosthetic joint thereby resists dislocation of the ball from the bearing liner cavity.

Although the present invention has been described in detail with reference to a preferred embodiment as shown in FIGS. 1–4, variations and modifications exist within the scope and spirit of the invention as described and defined in the following claims.

What is claimed is:

1. A bearing component for a ball-and-socket joint prosthesis, the bearing component comprising
   a bearing liner defined by an inner and outer surface and formed with a rim defining an opening to a concave bearing surface describing more than a hemisphere, and means formed in the rim between the inner and outer surfaces for permitting generally radially outward elastic deformation of the bearing surface adjacent the rim, the outward deformation selectively radially enlarging the opening to the concave bearing surface, and
   a locking component configured to couple the permitting means to inhibit the generally radially outward elastic deformation of the bearing surface around the rim.

2. The bearing component of claim 1, wherein the bearing liner has a lip that extends generally radially outwardly from the rim of the bearing liner.

3. The bearing component of claim 2, wherein a bearing liner ramp connects the lip bearing liner lip to the rim of the bearing liner.

4. The bearing component of claim 2, wherein the permitting means comprises a circular channel in the lip radially outward of the rim of the bearing liner, the channel formed so that the bearing liner has a thin portion around the rim to permit a ball with a diameter generally equal to a diameter of the concave bearing surface to pass through the rim as the thin portion deflects.

5. The bearing component of claim 4, wherein the locking component comprises a securing ring formed to fit inside the channel in the lip.

6. The bearing component of claim 5, wherein the bearing liner and securing ring are made from ultra high molecular weight polyethylene.

7. The bearing component of claim 1, wherein the bearing surface is generally spherical in shape and the bearing liner has a convex outer surface generally concentric with the concave bearing surface.

8. The bearing component of claim 7, wherein a flange extends outwardly from the convex outer surface of the bearing liner.

9. The bearing component of claim 7, wherein a groove extends around the convex outer surface of the bearing liner.

10. The bearing component of claim 1, wherein the permitting means comprises the bearing liner being formed sufficiently thin around the rim to permit a ball with a diameter generally equal to the diameter of the concave bearing surface to pass through the rim upon deflection of the bearing surfaces around the rim.

11. The bearing component of claim 10, wherein the locking component is formed to fit around the rim.

12. A bearing component for a ball-and-socket joint prosthesis, the bearing component comprising
    a bearing liner formed with a rim defining an opening, the rim connected to a concave bearing surface defining a bearing liner cavity that describes more than a hemisphere, a lip extending around the bearing liner rim, a channel formed in the lip defining a first radial inner and a second radial outward outer surface to permit outward elastic deformation of the bearing liner out radially the rim sufficient to allow a ball prosthesis with generally the same diameter as the bearing liner cavity to enter the bearing liner cavity, and
    a securing ring formed to fit in the channel to inhibit the radial outward elastic deformation of the bearing liner around the rim after insertion of the securing ring into the channel.

13. The bearing component of claim 12, wherein the bearing has a ramp, a bevel connects the bearing liner rim to the lip of the bearing liner.

14. The bearing component of claim 12, wherein the bearing surface is generally spherical in shape and the bearing liner has a convex outer surface generally concentric with the concave bearing surface.

15. The bearing component of claim 14, further comprising means for retaining the bearing component at a fixed position in a socket housing.

16. The bearing component of claim 15, wherein the retaining means comprises a flange extending from the convex outer surface of the bearing liner.

17. The bearing component of claim 16, wherein the retaining means further comprises a groove extending around the convex outer surface of the bearing liner, the groove formed adjacent a groove in the socket housing when the bearing component is fully inserted in the socket housing, and a lock wire situated in the adjacent grooves retains the bearing component in the socket housing.

18. The bearing component of claim 17, wherein the bearing liner and securing ring are made from ultra high molecular weight polyethylene.

19. A bearing liner assembly for a hip joint prosthesis having a femoral ball, the bearing liner assembly comprising:
    a bearing liner having an inner articular surface forming a greater than hemispherical cavity for receiving the femoral ball, an outer face formed to include a channel defining first radially inner and second radially outer concentric extensions, the first extension forming an integral portion of the inner articular surface and being outwardly flexible into the channel and toward the second extension upon introduction of the femoral ball into the cavity, and
    means for securing the ball within the bearing liner cavity by restricting the first extension against radially outward movement.

20. The bearing liner assembly of claim 19, wherein the securing means comprises a securing ring insertable into the channel.

21. The bearing liner assembly of claim, 20, wherein the distance from the inner articular surface to an outer surface of the securing ring is greater than the width of the channel.

22. The bearing liner assembly of claim 20, wherein the bearing liner and securing ring are made from ultra high molecular weight polyethylene.

23. The bearing liner assembly of claim 19, wherein the bearing liner is generally hemispherical in shape and has an outer surface concentric with the inner articular surface.

24. The bearing liner assembly of claim 23, wherein the inner articular surface forms a general hemisphere that covers more than half of the femoral ball when the femoral ball is inserted into the cavity of the bearing liner.

25. A bearing liner assembly for a hip joint prosthesis having a femoral ball, the bearing liner assembly comprising a bearing liner having an inner articular surface forming a greater than hemispherical cavity for receiving the femoral ball, an outer face formed to include a concentric channel having a radial inner and a radial outer wall, the radially inner wall of the bearing liner, adjacent the face being flexible radially outwardly into the channel to permit the femoral ball to be inserted into the cavity, and a securing ring formed for insertion into the channel to restrict the radially outward movement of the radially inner wall of the channel.

26. A bearing component for a ball-and-socket joint prosthesis, the bearing component comprising:

a one-piece bearing liner defined by an outer surface and an inner concave spherical bearing surface describing a spherical cavity of more than 180 degrees and with a rim surface extending between the outer and inner surfaces to define an end surface of the bearing liner and an opening into the inner spherical concave bearing surface; a channel extending into the bearing liner from the rim surface between the inner and outer surfaces, for providing a space for outward deformation of an end portion of the inner concave surface, located adjacent the opening, toward an area of the outer surface adjacent the rim end surface.

27. The bearing component of claim 26 wherein the channel is sized to receive a blocking member therein to inhibit the outward deformation.

28. The bearing component of claim 26 wherein the channel extends completely around the rim surface to form a circular channel.

29. The bearing component of claim 26 wherein the channel dimension along the rim surface is wide enough to allow deflection of the end portion of the inner concave surface such that the opening to the inner spherical cavity is enlarged sufficiently to change the configuration of the inner spherical cavity to define at least a hemisphere cavity.

30. The bearing component of claim 26 wherein a shape of the end portion of the inner concave surface causes a distance between the inner concave surface and a side wall of the channel to vary from the rim surface to a bottom of the channel.

31. The bearing component of claim 26 wherein the distance at the bottom of the channel is larger than the distance at the rim surface.

32. The bearing component of claim 26 wherein a cross-sectional area of the end portion of the inner concave surface is ramped shaped so as to provide a uniform rate of distance increase.

33. The bearing component of claim 26 wherein a flange extends outwardly from the outer surface of the bearing liner.

34. The bearing component of claim 26 wherein a groove extends around the outer surface of the bearing liner.

35. The bearing component of claim 26 wherein the bearing liner cavity is sized to snugly receive a femoral ball of a hip joint prosthesis.

* * * * *